United States Patent [19]

Kulik et al.

[11] Patent Number: 4,784,137
[45] Date of Patent: Nov. 15, 1988

[54] SURGICAL SUTURING INSTRUMENT

[76] Inventors: Yaroslav P. Kulik, ulitsa Zeiskaya, 140, kv. 36, Blagoveschensk; Ivan I. Shmyrin, prospekt Krasnogo Znameni, 30, kv. 132, Vladivostok, both of U.S.S.R.

[21] Appl. No.: 127,031

[22] Filed: Nov. 16, 1987

[51] Int. Cl.$^4$ .......................... A61B 17/04; B31B 1/68
[52] U.S. Cl. .................................. 128/334 R; 227/19
[58] Field of Search ............ 128/334 R; 227/DIG. 1, 227/19

[56] References Cited

U.S. PATENT DOCUMENTS

| | | | |
|---|---|---|---|
| 4,111,206 | 9/1978 | Vishnevsky et al. | 227/19 |
| 4,402,444 | 9/1983 | Green | 227/19 |
| 4,573,622 | 3/1986 | Green et al. | 227/19 |
| 4,610,383 | 9/1986 | Rothfuss et al. | 227/19 |
| 4,648,542 | 3/1987 | Fox et al. | 227/19 |

FOREIGN PATENT DOCUMENTS 125867 7/1967 U.S.S.R. .......................... 128/334 R

Primary Examiner—Richard C. Pinkham
Assistant Examiner—Gary Jackson
Attorney, Agent, or Firm—Lilling & Greenspan

[57] ABSTRACT

A surgical suturing instrument comprises hinge-joined a staple jaw provided with staple slots, and a supporting jaw provided with depressions for the staple legs to bend, a mechanism for ejecting the staples from the slots, a mechanism for turning the supporting jaw with respect to the staple jaw, and a mechanism for fixing the jaws in the drawn-together position. The supporting jaw is located at the end of the staple jaw so as to rotate, in a hinge-joint, through 180 degrees with respect to the latter.

2 Claims, 7 Drawing Sheets

SURGICAL SUTURING INSTRUMENT

FIELD OF THE INVENTION

The invention relates generally to medical engineering and more specifically it concerns a surgical suturing instrument adapted predominantly for laparoscopic appendectomy.

BACKGROUND OF THE INVENTION

Widespread acceptance has been gained in the recent years by such laparoscopic surgical procedures as cholecystomy, gastrostomy, sterilization, appendectomy.

Widely known in also application of surgical suturing instruments in cardiovascular and pulmonary surgery, as well as in operative interventions on the gastrointestinal tract, since such instruments are capable of providing a staunch suture and cutting down the operating time. However, none of the heretofore-known suturing instruments is suitable for endoscopic application.

Thus, one prior-art surgical suturing instrument for establishing lateral gastrointestinal anastomoses is known (SU, A, 125,867) to comprise hinge-joined a staple jaw provided with slots for staples and having a handle at one of its ends, and a supporting jaw provided with depressions for the staple legs to bend, a mechanism for staple ejection from the slots, and a mechanism for fixing the jaws in the drawn-together position. In said known instrument the hinge joint interconnecting the jaws is located at the end of the staple jaw handle. With the instrument in the drawn-apart position the jaws make up an angle with each other, whereby the surgical instrument in question is inapplicable for endoscopic manipulations.

SUMMARY OF THE INVENTION

It is an object of the invention to render appendectomy practicable with the aid of a surgical suturing instrument.

It is another object of the invention to bring an improvement in the heretofore-known surgical suturing instrument aimed at enabling its introduction into the zone of surgery through the guide tube of a laparoscopic wound retractor.

It is one more object of the invention to render appendectomy less traumatic.

The essence of the invention resides in the fact that in a surgical suturing instrument, comprising hinge-joined a staple jaw provided with staple slots and having a handle at one of its ends, and a supporting jaw provided with depressions for the staple legs to bend, a mechanism for staple ejection from the slots, and a mechanism for fixing the jaws in the drawn-together position, according to the invention, the hinge joint interconnecting the jaws is located at the vacant end of the staple jaw, the supporting jaw is connected to the hinge joint through one of its ends and mounted rotatably through 180 degrees in such a manner that, when the instrument is in the drawn-apart position, the supporting jaw is in fact an extension to the staple jaw, and when the instrument is in the drawn-together position, the supporting jaw is arranged parallel to the staple jaw, said supporting jaw being provided with a turning mechanism made as a lever whose pivot pin is located on the handle of the staple jaw, and a link connected to the lever and to the supporting jaw.

It is expedient that the mechanism for fixing the jaws in the drawn-together position be made as a clamp located on the supporting jaw, and an actuator located on the handle and adapted, by virtue of a force applied thereto, to interact with a rack which is associated with wedgelike members mounted slidably along the staple jaw so as to lock, with the aid of the clamp, the supporting jaw with respect to the staple jaw in the drawn-together position of the instrument.

The surgical suturing instrument, according to the invention, makes it possible to perform appendectomy by the laparoscopic technique, without slitting the abdominal cavity open but through punctures made in the abdominal wall, which makes the surgery less traumatic. The instrument is convenient in handling and provides for highly dependable closure of the appendicular stump after appendectomy.

BRIEF DESCRIPTION OF THE DRAWINGS

In what follows the invention is illustrated in a description of its specific embodiments with reference to the accompanying drawings, wherein according to the invention.

DETAILED DESCRIPTION OF THE INVENTION

Figure 1:
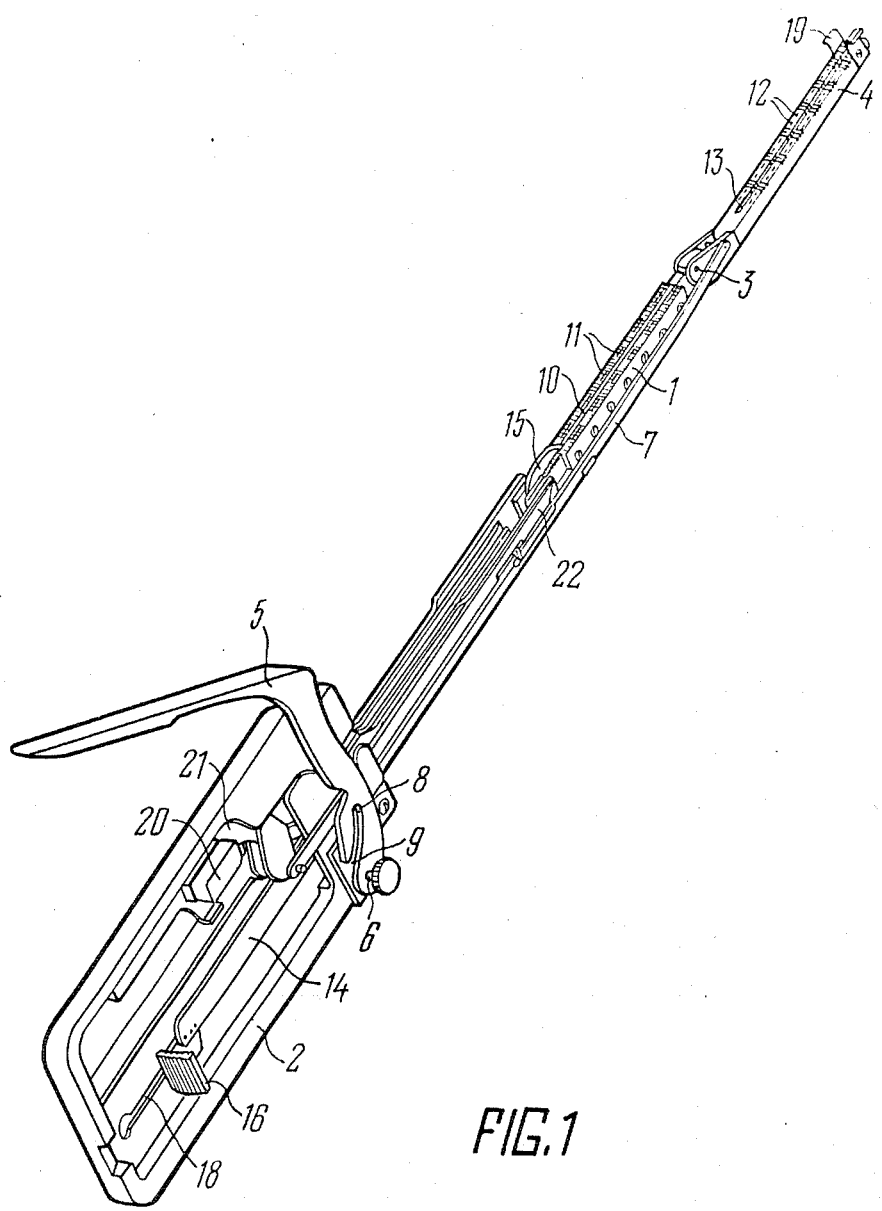
FIG. 1 is an isometric view of a surgical suturing instrument when in the drawn-apart position.
Figure 3:
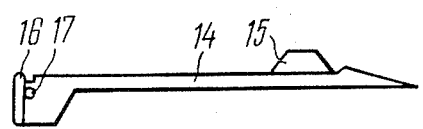
FIG. 3 is a side view of the actuator of a mechanism for staple ejection from the slots.
Figure 2:
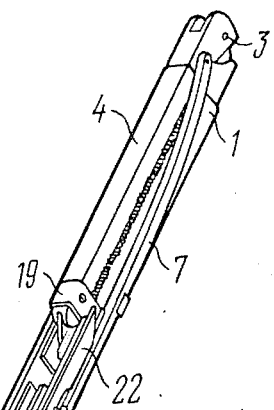
FIG. 2 shows the instrument of FIG. 1 when in the drawn-together position.
Figure 2:
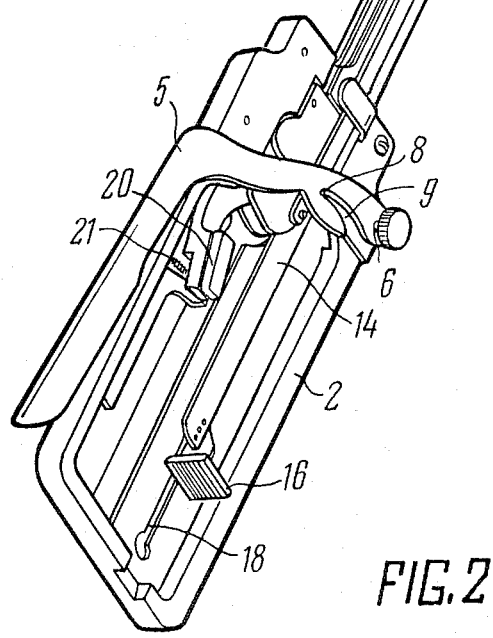

The surgical suturing instrument as shown in FIGS. 1 and 2, comprises a staple jaw 1 having a handle 2 at one of its ends and a hinge joint 3 at the opposite end, and a supporting jaw 4 which is connected, through one of its ends, to the staple jaw 1 by means of the hinge joint 3. The supporting jaw 4 to turnable through 180 degrees with respect to the staple jaw 1. When in one of its extreme positions the jaw 4 is in fact an extension to the staple jaw 1 (with the instrument in the drawn-apart position as shown in FIG. 1), and when in the other extreme position the jaw 4 is set parallel to the staple jaw 1 (with the instrument in the drawn-together position as shown in FIG. 2). The supporting jaw 4 is provided with a turning mechanism made as a lever 5 whose pivot pin 6 is located on the handle 2, and a link 7 which is connected, through one of its ends, to the supporting jaw 4, while its other end carries a pin 8 adapted to engage a recess 9 in the lever 5. The staple jaw 1 has a longitudinal slit 10 and a number of slots 11 arranged on both sides of the slit 10 and adapted to accommodate pi-shaped staples made of, e.g., tantalum wire and measuring $0.2 \times 3 \times 4$ mm each. Located on the supporting jaw 4 in opposition to the slots 11 of the staple jaw 1 are two rows of depressions 12 adapted for the staple legs to bend during suturing, and a longitudinal slot 13 in corresponding opposition to the longitudinal slit 10 of the staple jaw 1. According to the invention, the instrument is provided with a mechanism for ejecting the staples from the slots 11, which is similar as for construction to the known mechanisms serving the same purpose. The mechanism incorporates staple ejector 14 (FIGS. 1, 3) pointed at one end, provided with a knife 15 and mounted movably along the slit 10 (FIG. 1), and movable members (omitted in the Drawing)

located in the slit 10 square with it and capable of traversing, under the action of the pointed end of the staple ejector 14, in their plane so as to expel the staples out of the slots 11. The end of the staple ejector 14 opposite to its pointed end carries a stop 16 and a pin 17 located in a guide slot 18 of the handle 2. In addition, the surgical suturing instrument of the invention comprises a mechanism for fixing the jaws 1, 4 in the drawn-together position, said mechanism being made as a clamp 19 located at the vacant end of the supporting jaw 4 and an actuator 20 located on the handle 2, a rack 21, and wedgelike members 22. The actuator 20 is adapted to interact, by virtue of a force applied thereto, with the toothed segment of the rack 21, while each of the wedgelike members 22 is secured, with one of its ends, to the toothed segment of the rack 21, and all the members 22 are mounted slidably along the staple jaw 1 so as to lock, with the aid of pointed ends of the members 22 and by means of the clamp 19, the supporting jaw 4 with respect to the staple jaw when the instrument is in the drawn-together position.

The surgical suturing instrument of the invention is applied according to the techniques described below with reference to a laparoscopic appendectomy. my. Prior to surgery one should place staples into the slots 11 of the jaw 1.

Then the laparoscope is introduced at the McBurney's point, and revision of the abdominal cavity is performed. The instrument is applicable whenever the appendix is adhesion-free, or at any rate lies in loose adhesions.

Figure 4:
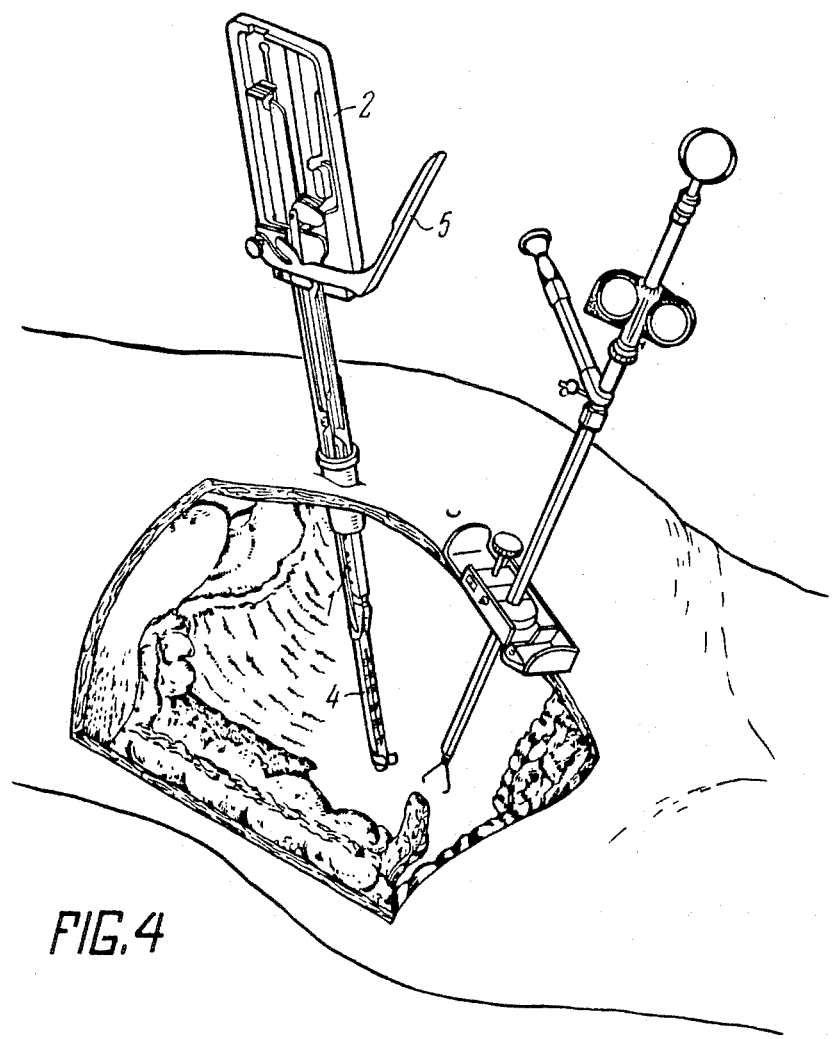
FIGS. 4 through 8 illustrate the various stages of appendectomy performed with the aid of the surgical suturing instrument as shown in FIGS. 1 and 2.
Figure 5:
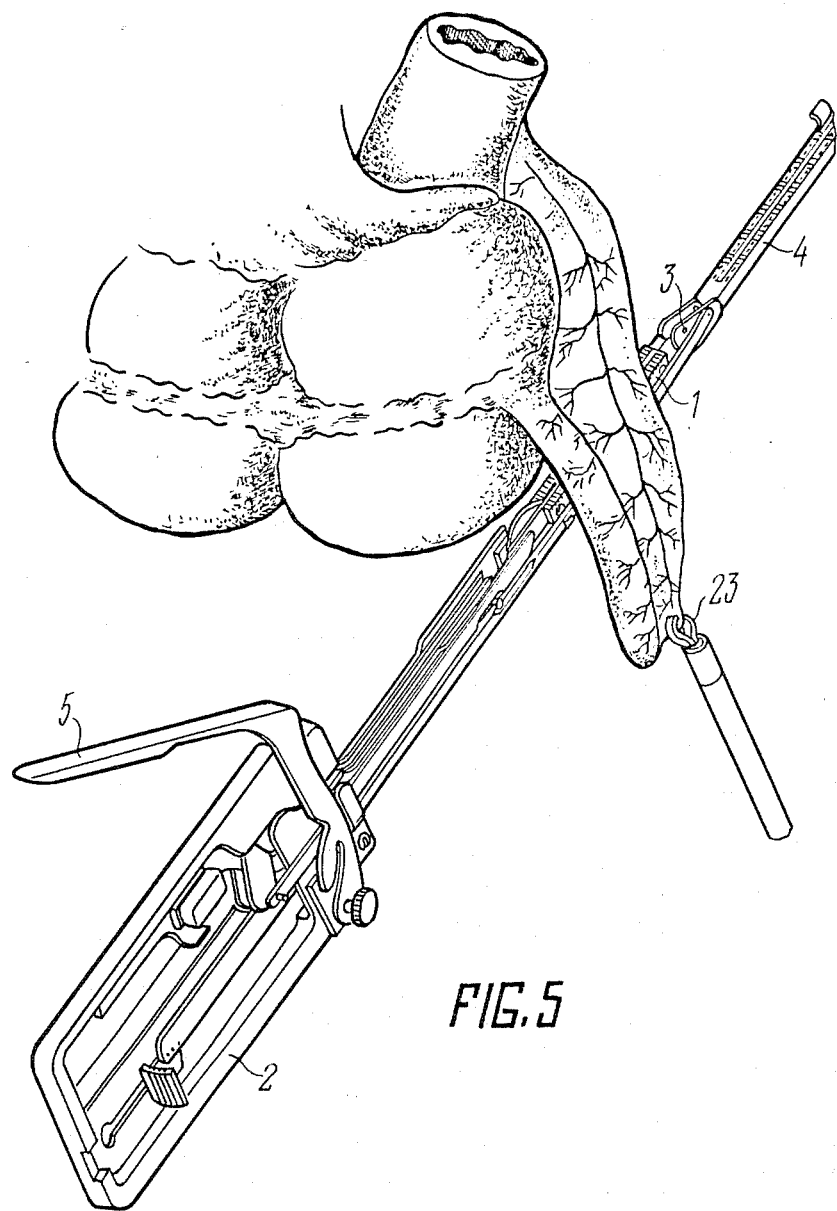
Figure 6:
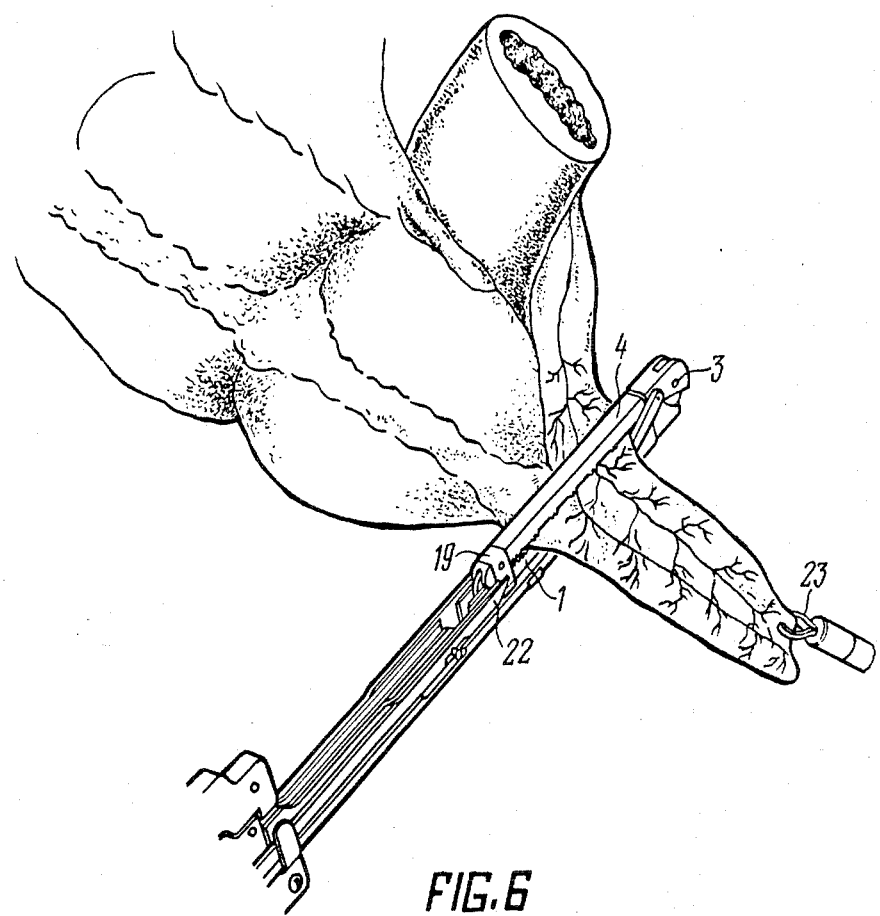
Figure 7:
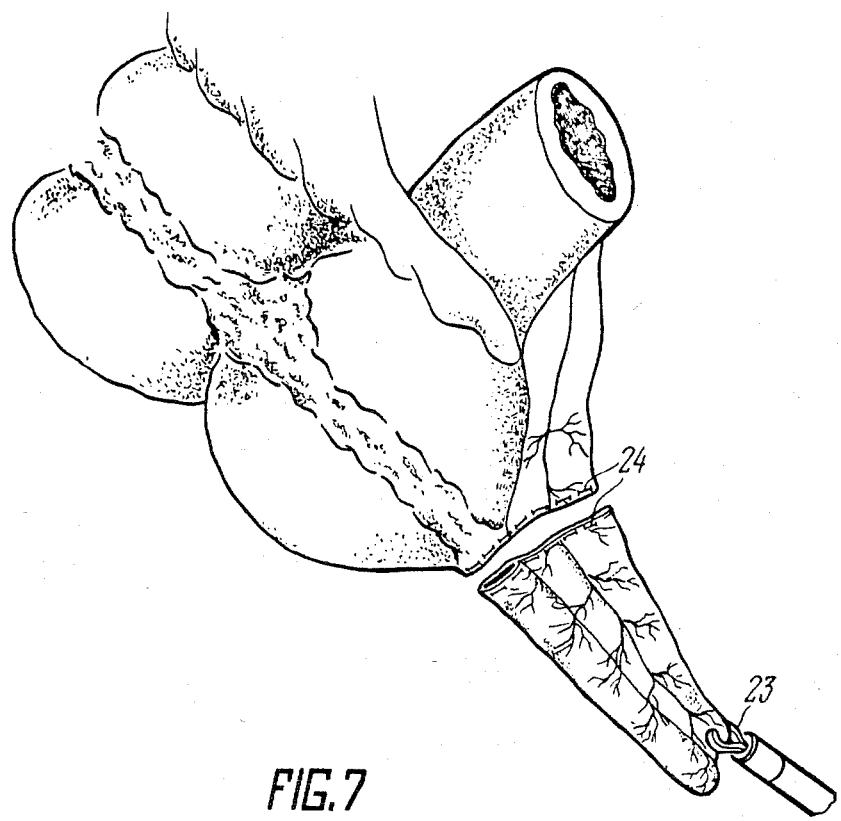
Figure 8:
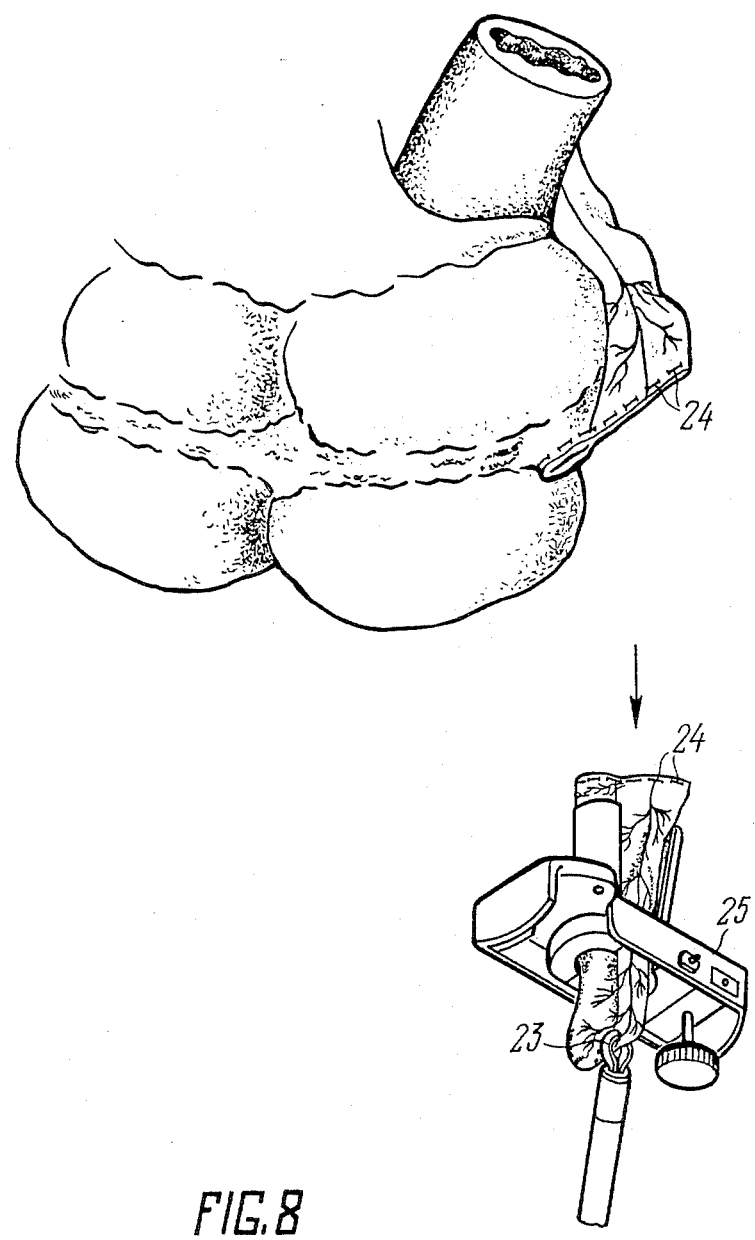

Proceeding from the laparoscopic findings the surgeon introduces, through a second puncture, the guide tube of a wound retractor, whereupon the surgical suturing instrument in the drawn-apart position (FIGS. 4, 5) is introduced into the abdominal cavity through the guide tube. Then the appendix is immobilized with a forceps 23 (FIG. 5) applied to its apex and introduced through the operating canal of the laparoscope, and the staple jaw 1 of the suturing instrument is brought under the base of the appendix and mesentery. Thereupon one should press the lever 5 of the handle 2 so as to cause the supporting jaw 4 to rotate in the hinge joint 3 through 180 degrees, thus changing the suturing instrument over into a drawn-together position. As a result, the supporting jaw 4 (FIGS. 2, 6) is set parallel to the staple jaw 1. Next the jaws 1, 4 are fixed in the drawn-together position, thus exerting a force on the actuator 20, with the result that the toothed segment of the rack 21 rotates and causes the wedge-like members 22 to advance towards the working end of the instrument. The members 22 act with their pointed ends upon the bent-out portions of the clamp 19, thus tightly pressing the jaws 1 and 4 against each other. Hence the base of the appendix and that of the mesentery get squeezed between the contact surfaces of the jaws 1 and 4. Then the surgeon should press the stop 16 (FIGS. 1, 2, 3) so as to push the staple ejector 14 with the knife 15 forward. As a result, the staple ejector 14 slides along the slit 10 and with its pointed end raises the members a little, which expel the staples out of the slots 11. The staples pierce with their legs the compressed walls of the appendix and both of the mesenteric folds, whereupon the blade of the knife 15 cuts across the appendix and mesentery between the two rows of staples 24 (FIG. 7). Thereupon the suturing instrument is brought apart by pressing the lever 5 (FIG. 1) and extracted from the abdominal cavity through the guide tube of the wound retractor. The cut-off appendix is removed from the abdominal cavity through a laparoscopic wound retractor 25 (FIG. 8) using the forceps 23.

Some experimental specimens of the present surgical suturing instrument have been manufactured and then trialled in experiments on human corpses and test dogs. All experiments have proved the instruments to be quite operable.

An exemplary application of the present surgical suturing instrument, is presented below.

Subject of experiment-corpse of male human K., aged 34 who succumbed to mechanical asphyxia on Apr. 6, 1986. Laparoscopy revealed the appendix lying medially, free from adhesions. Appendectomy was performed with the aid of the surgical suturing instrument of the invention. Laparotomy was performed involving ligation of the ileum and application of a clamp to the ascending colon. Then the pressure in the cecum was raised to 90 mm Hg to test the suture of the appendicular stump for tightness. The appendicular stump suture remained tight and staunch under the aforesaid pressure values.

Thus the surgical suturing instrument, according to the invention, makes it possible to perform appendectomy by the laparoscopic technique which makes the surgery less traumatic and more safe.

What is claimed is:

1. A surgical suturing instrument, comprising:
    a staple jaw shaped as a rod having a first working end and a second end;
    a handle of said staple jaw located at said second end opposite to said working end of the staple jaw;
    a hinge joint located at said working end of said staple jaw;
    a supporting jaw shaped as a rod having a first end and a second end, and associated with said staple jaw through said first end by means of said hinge joint;
    said hinge joint enabling said supporting jaw to rotate through 180 degrees with respect to said staple jaw so that when said suturing instrument is in the drawn-apart position, said supporting jaw is in fact an extension to said staple jaw, and when said suturing instrument is in the drawn-together position, said supporting jaw is set parallel to said staple jaw;
    a mechanism for turning said supporting jaw relative to said staple jaw;
    a lever of said turning mechanism, having a pivot pin located on said handle;
    a link of said turning mechanism, having a first end and a second end, said link being held, through said first end, to the arm of said lever and through said second end, to said supporting jaw;
    slots adapted to accommodate staples and located at said working end of said staple jaw;
    depressions for bending the legs of said staples, located on said supporting jaw, the number of said depressions being equal to the number of said slots, each of said depressions being arranged opposite to said respective slot when said instrument is in said drawn-together position;
    a mechanism for ejecting said staples from said slots;
    a mechanism for fixing said staple jaw and said supporting jaw in a position parallel to each other when the instrument is in said drawn-together position.

2. A surgical suturing instrument as claimed in claim 1, wherein said mechanism for fixing said jaws in a position parallel to each other comprises:
- a clamp located on said supporting jaw;
- an actuator located on said handle adapted for reciprocating motion;
- a rack located on the handle and having a toothed segment which is capable of smoothly rotating when acted upon by said actuator;
- a first oblong wedgelike member and a second oblong wedgelike member, each having a first pointed end and a second end, said wedgelike members being held through said second ends thereof, to said toothed segment of the rack, and being arranged on the opposite sides of said staple jaw length-wise the latter adapted to slide along said staple jaw during said rotation of said toothed segment so as to lock, with their said pointed ends upon interacting with said clamp, said supporting jaw with respect to said staple jaw in a position where said supporting jaw is set parallel to said staple jaw

* * * * *